United States Patent [19]

Bernardon

[11] Patent Number: 6,156,788

[45] Date of Patent: Dec. 5, 2000

[54] POLYCYCLIC AROMATIC COMPOUNDS AND PHARMACEUTICAL/COSMETIC COMPOSITIONS COMPRISED THEREOF

[75] Inventor: Jean-Michel Bernardon, Le Rouret, France

[73] Assignee: Centre International de Recherches Dermatologiques Galderma, Valbonne, France

[21] Appl. No.: 09/369,875

[22] Filed: Aug. 9, 1999

Related U.S. Application Data

[63] Continuation of application No. 08/971,983, Nov. 17, 1997, which is a continuation of application No. 08/429,096, Apr. 26, 1995, Pat. No. 5,766,610.

[30] Foreign Application Priority Data

Apr. 26, 1994 [FR] France ................................ 94 05019

[51] Int. Cl.$^7$ .................... C07D 327/06; C07D 409/00; C07D 333/32; C07D 333/34
[52] U.S. Cl. ............................. 514/444; 549/23; 549/60; 549/62; 549/63; 549/64; 549/65; 549/66; 549/68
[58] Field of Search ...................... 514/432, 434, 514/444, 445, 447, 233.5, 233.8, 231.5, 252, 320, 321, 253, 319, 422, 376, 377; 549/15, 23, 60, 62, 63, 64, 65, 66, 68; 544/146, 379; 546/196, 197, 202, 205, 206; 548/527, 525, 526; 530/331

[56] References Cited

U.S. PATENT DOCUMENTS

| | | | |
|---|---|---|---|
| 5,087,743 | 2/1992 | Jansen et al. | 562/466 |
| 5,766,610 | 6/1998 | Bernardon | 424/401 |

FOREIGN PATENT DOCUMENTS

| | | |
|---|---|---|
| 0386452 | 9/1990 | European Pat. Off. . |
| 76838 /3 | 10/1985 | Israel . |

OTHER PUBLICATIONS

Green, John W., Classification of Blocking Groups, Methods in Carbohydrate Chem. Eds. Whistler, R.L, Wolfrom, M.L. BeMiller, J.N. vol. II, Reactions of Carbohydrates, pp. 3–8, 1963.

*Primary Examiner*—Mukund J. Shah
*Assistant Examiner*—Ben Schroeder

*Attorney, Agent, or Firm*—Burns, Doane, Swecker & Mathis, L.L.P.

[57] ABSTRACT

Novel pharmaceutically/cosmetically-active polycyclic aromatic compounds have the structural formula (I):

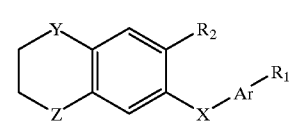

(I)

wherein Ar is a radical having one of the formulae (a)–(e):

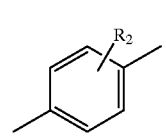

(a)

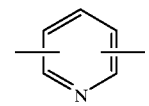

(b)

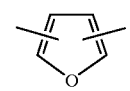

(c)

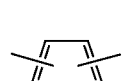

(d)

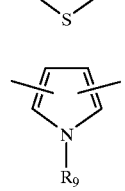

(e)

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

47 Claims, 1 Drawing Sheet

POLYCYCLIC AROMATIC COMPOUNDS AND PHARMACEUTICAL/COSMETIC COMPOSITIONS COMPRISED THEREOF

CROSS-REFERENCE TO COMPANION APPLICATIONS

This application is a continuation of Ser. No. 08/971,983 filed Nov. 17, 1997 which is a continuation of Ser. No. 08/429,096 filed Apr. 26, 1995, now U.S. Pat. No. 5,766,610.

Copending applications Ser. No. 08/429,492 and Ser. No. 08/429,045, both filed Apr. 26, 1995, and assigned to the assignee hereof. Cf. copending applications Ser. No. 08/356,913, each filed Dec. 15, 1994, and each also assigned to the asignee hereof.

BACKGROUND OF THE INVENTION

Technical Field of the Invention

The present invention relates to novel polycyclic aromatic compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and proliferation and are particularly useful in the topical and systemic treatment of dermatological conditions associated with a keratinization disorder, dermatological conditions (and the like) including an inflammatory and/or immunoallergic component, and dermal or epidermal proliferations, whether benign or malignant. The subject compounds can, in addition, be used for the treatment of degenerative diseases of the connective tissue, for combating skin aging, whether photoinduced or chronologic, and for treating cicatrization or healing disorders. Moreover, they are also useful for ophthalmological applications, especially for the treatment of corneopathies. In general, they are useful for the treatment of any disease state which is associated with a modification in the expression of receptors belonging to the superfamily of steroid and thyroid hormone receptors.

Too, the compounds according to this invention can also be formulated into cosmetic compositions for body and hair care/hygiene.

Briefly, the polycyclic aromatic compounds according to this invention have the following structural formula (I):

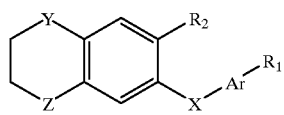

(I)

in which R, is a hydrogen atom, a —CH$_3$ radical, a —CH$_2$—O—R$_3$ radical, a —CH$_2$—O—CO—R$_4$ radical, an —O—R$_5$ radical, an —O—(—CH$_2$-) -$_m$- (—CO—) -$_n$-R$_6$ radical, a —CO—R$_7$ radical, a —CO—O—R$_8$ radical or an —S(O)$_p$—R$_9$ radical, wherein m, n, p and the radicals R$_3$ to R$_9$ are as defined below; R$_2$ is a hydrogen atom or a halogen atom, a lower alkyl radical, an —NO$_2$ radical, an —O—COR$_4$ radical, an —OR$_9$ radical or a radical

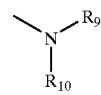

wherein the radicals R$_4$, R$_9$ and R$_{10}$ are as defined below; Ar is a radical selected from among those of the following formulae (a)–(e):

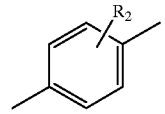

(a)

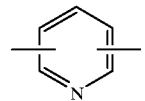

(b)

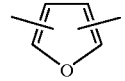

(c)

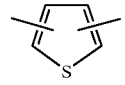

(d)

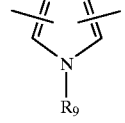

(e)

X is —O—, —S (O)$_t$- or an —NR$_9$- radical wherein t is as defined below; Y and Z are each —O—, —S(O)$_t$- or a radical —CR$_{11}$R$_{12}$, wherein the radicals R$_{11}$ and R$_{12}$ are as defined below; m is an integer equal to 1, 2 or 3; n is an integer equal to 0 or 1; p is an integer equal to 0, 1, 2 or 3; t is an integer equal to 0, 1 or 2; R$_3$ is a hydrogen atom or a lower alkyl radical; R$_4$ is a lower alkyl radical; R$_5$ is a hydrogen atom or a lower alkyl radical; R$_6$ is a lower alkyl radical or a heterocycle; R$_7$ is a hydrogen atom, a lower alkyl radical or a radical:

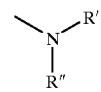

in which R' and R", which may be identical or different, are each a hydrogen atom, a lower alkyl radical, a mono- or polyhydroxyalkyl radical, an optionally substituted aryl radical, or an amino acid or peptide or sugar residue, with the proviso that R' and R" may together form, with the nitrogen atom from which they depend, a nitrogen-containing heterocycle; R$_8$ is a hydrogen atom, a linear or branched alkyl radical having from 1 to 20 carbon atoms, an alkenyl radical, a mono-or polyhydroxyalkyl radical, an optionally substituted aryl or aralkyl radical, or a sugar residue or an amino acid or peptide residue; R$_9$ is a hydrogen atom or a lower alkyl radical; R$_{10}$ is a hydrogen atom or a lower alkyl radical; R$_{11}$ is a hydrogen atom or a lower alkyl radical; R$_{12}$ is a hydrogen atom or a lower alkyl radical; with the proviso that Y and Z cannot at the same time each be an oxygen atom or an —S(O)t- radical.

This invention also features the salts of the compounds of formula (I) above in the event that the radical $R_1$ represents a carboxylic acid functional group or a sulfonic acid functional group, or bears an amine functional group, or, alternatively, when the radical $R_2$ represents an amine functional group, as well as the chiral and geometric isomers thereof. When the compounds according to the invention exist in the form of salts, they are preferably salts of an alkali or alkaline earth metal, or, alternatively, of zinc or of an organic amine.

BRIEF DESCRIPTION OF THE DRAWING

The FIGURE of Drawing sets forth reaction schemes/mechanisms illustrating representative syntheses for the preparation of the polycyclic aromatic compounds according to the present invention.

DETAILED DESCRIPTION OF BEST MODE AND PREFERRED EMBODIMENTS OF THE INVENTION

Figure 1:
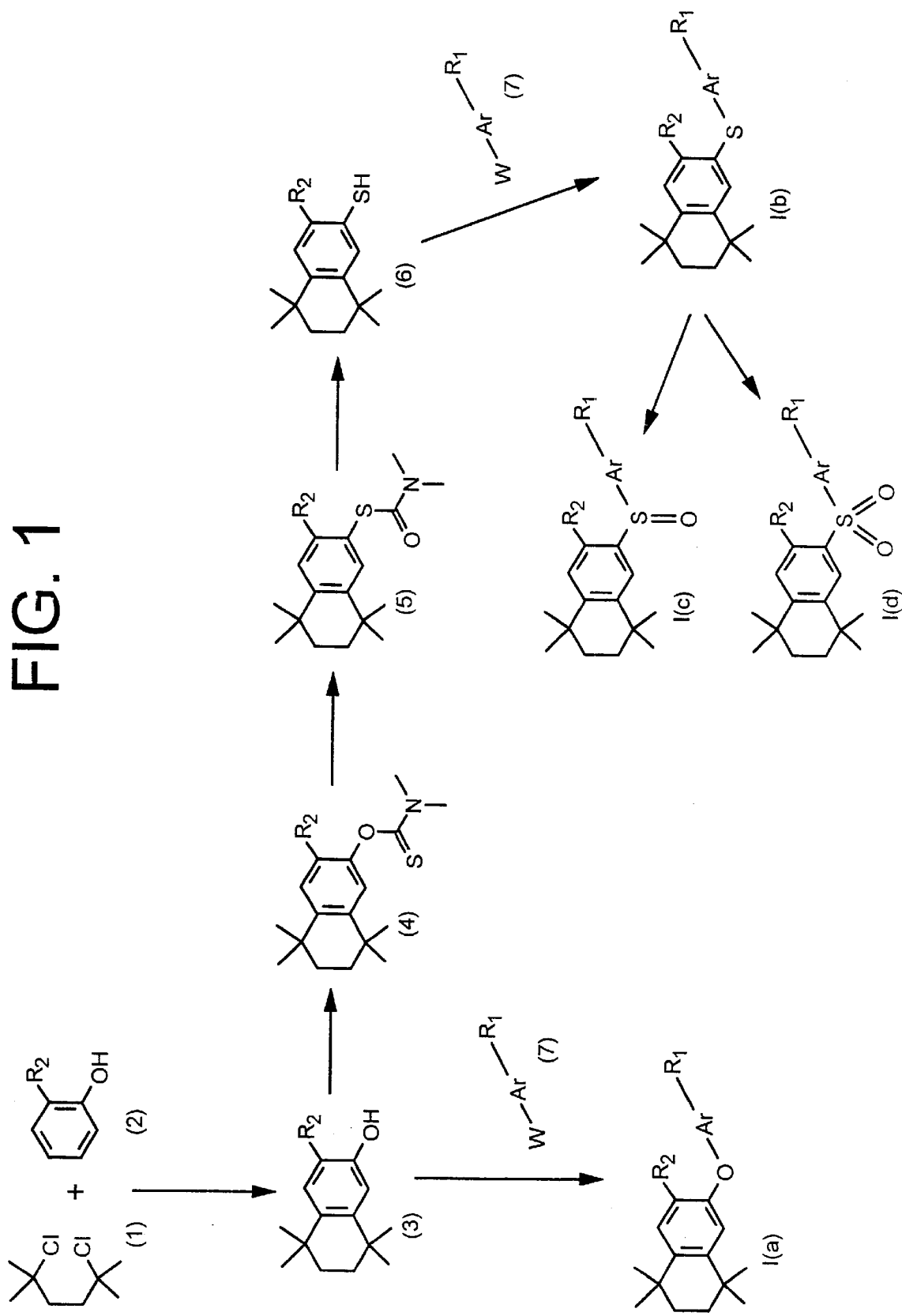

More particularly according to the present invention, by the term "lower alkyl radical" is intended a radical having from 1 to 6 carbon atoms, preferably methyl, ethyl, isopropyl, butyl, tert-butyl and hexyl radicals.

By the term "linear or branched alkyl radical having from 1 to 20 carbon atoms" is preferably intended methyl, ethyl, propyl, 2-ethylhexyl, octyl, dodecyl, hexadecyl and octadecyl radicals.

By the term "monohydroxyalkyl radical" is intended a radical preferably having 2 or 3 carbon atoms, especially a 2-hydroxyethyl, 2-hydroxypropyl or 3-hydroxypropyl radical.

By the term "polyhydroxyalkyl radical" is intended a radical preferably having from 3 to 6 carbon atoms and 2 to 5 hydroxyl groups, such as 2,3-dihydroxypropyl, 2,3,4-trihydroxybutyl or 2,3,4,5-tetrahydroxypentyl radicals or pentaerythritol residue.

By the term "aryl radical" is preferably intended a phenyl radical optionally substituted by at least one halogen atom, or a hydroxyl or nitro functional group.

By the term "aralkyl radical" is preferably intended a benzyl or phenethyl radical optionally substituted by at least one halogen atom, or a hydroxyl or nitro functional group.

By the term "alkenyl radical" is intended a radical preferably having from 2 to 5 carbon atoms and one or more sites of ethylenic unsaturation, such as, more particularly, the allyl radical.

By the term "sugar residue" is intended a residue derived especially from glucose, galactose or mannose, or alternatively from glucuronic acid.

By the term "amino acid residue" is especially intended a residue derived from lysine, glycine or aspartic acid, and by "peptide residue" is more particularly intended a dipeptide or tripeptide residue prepared via the combination of amino acids.

Lastly, by the term "heterocycle" is preferably intended a piperidino, morpholino, pyrrolidino or piperazino radical, optionally substituted in the 4-position by a $C_1$–$C_6$ alkyl radical or a mono- or polyhydroxyalkyl radical as defined above.

When the radical $R_2$ is a halogen atom, it is preferably a fluorine, chlorine or bromine atom.

Among the compounds of formula (I) according are the following:

4-(5,6,7,8-Tetrahydro-5,5,8,8-tetramethyl-2-naphthyloxy)benzoic acid;

4-(5,6,7,8-Tetrahydro-5,5,8,8-tetramethyl-2-naphthylthio)benzoic acid;

4-(5,6,7,8-Tetrahydro-5,5,8,8-tetramethyl-2-naphthylsuifinyl)benzoic acid;

4-(5,6,7,8-Tetrahydro-5,5,8,8-tetramethyl-2-naphthylsulfonyl)benzoic acid;

4-(5,6,7,8-Tetrahydro-5,5,8,8-tetramethyl-2-naphthylamino)benzoic acid;

5-(5,6,7,8-Tetrahydro-5,5,8,8-tetramethyl-2-naphthylthio)-2-thiophene carboxylic acid;

4-(3,5,5,8,8-Pentamethyl-5,6,7,8-tetrahydro-2-naphthyloxy)benzoic acid;

4-(3,5,5,8,8-Pentamethyl-5,6,7,8-tetrahydro-2-naphthylthio)benzoic acid;

4-(3-Ethyl-5,5,8,8-tetramethyl-5,6,7,8-tetrahydro-2-naphthyloxy)benzoic acid;

4-(3-Isopropyl-5,5,8,8-tetramethyl-5,6,7,8-tetrahydro-2-naphthyloxy)benzoic acid;

4-(5,6,7,8-Tetrahydro-5,5,8,8-tetramethyl-2-naphthyloxy)acetophenone;

4-(5,6,7,8-Tetrahydro-5,5,8,8-tetramethyl-2-naphthyloxy)benzaldehyde;

4-(3-Bromo-5,6,7,8-tetrahydro-5,5,8,8-tetramethyl-2-naphthyloxy)benzoic acid;

3-Methyl-4-(5,6,7,8-tetrahydro-5,5,8,8-tetramethyl-2-naphthylthio)benzoic acid;

3-Methyl-4-(3,5,5,8,8-pentamethyl-5,6,7,8-tetrahydro-2-naphthylthio)benzoic acid;

3-Methyl-4-(3-ethyl-5,6,7,8-tetrahydro-5,5,8,8-tetramethyl-2-naphthyloxy)benzoic acid;

6-(3,5,5,8,8-Pentamethyl-5,6,7,8-tetrahydro-2-naphthylthio)nicotinic acid;

2-Hydroxy-4-(3,5,5,8,8-pentamethyl-5,6,7,8-tetrahydrol-2-naphthylthio)benzoic acid;

2-Chloro-4-(3,5,5,8,8-pentamethyl-5,6,7,8-tetrahydro-2-naphthylthio)benzoic acid;

4-(3-Ethyl-5,6,7,8-tetrahydro-5,5,8,8-tetramethyl-2-naphthylthio)benzoic acid;

4-(3-Isopropyl-5,6,7,8-tetrahydro-5,5,8,8-tetramethyl-2-naphthylthio)benzoic acid;

4-(3-n-Propyl-5,6,7,8-tetrahydro-5,5,8,8-tetramethyl-2-naphthylthio)benzoic acid;

4-(3,5,5,8,8-Pentamethyl-5,6,7,8-tetrahydro-2-naphthylthio)benzenemethanol;

4-(3,5,5,8,8-Pentamethyl-5,6,7,8-tetrahydro-2-naphthylthio)benzaldehyde;

N-Ethyl-4-(3,5,5,8,8-pentamethyl-5,6,7,8-tetrahydro-2-naphthylthio)benzamide;

N-4-Hydroxyphenyl-4-(3,5,5,8,8-pentamethyl-5,6,7,8-tetrahydro-2-naphthylthio)benzamide.

According to the present invention, the more particularly preferred compounds of formula (I) are those in which at least one, and preferably all, of the conditions given below are satisfied:

$R_1$ is a —CO—$R_7$ radical;

$R_2$ is a lower alkyl radical or an —$OR$, radical;

Ar is a radical of formula (a); and

X is —O—, —S— or —$NR_9$—.

The present invention also featues the processes for the preparation of the compounds of formula (I), in particular via to the reaction schemes illustrated in the FIGURE of Drawing.

Thus, the compounds of formula I (a) can be prepared (FIGURE of Drawing) from the sodium salt of the phenolic derivative (3) by coupling with a halogenated derivative (7), preferably a bromine-containing or iodine-containing derivative, in the presence of a copper bromide and dimethyl sulfide complex in a solvent such as pyridine. The phenolic derivatives (3) can in turn be obtained by a Friedel-Crafts type reaction from a phenol (2) and a dihalogenated derivative (1) in the presence of a Lewis acid, for example aluminum chloride.

The compounds of formula I (b) can be obtained (also the FIGURE of Drawing) from the sodium salt of the thiol derivative (6) by coupling with a halogenated derivative (7), preferably a bromine-containing or iodine-containing derivative, in the presence of a catalyst such as certain transition metal complexes, in an alcoholic solvent such as ethyl or butyl alcohol. As exemplary suitable catalysts include, in particular, those derived from nickel or palladium, for example $Ni^{II}$ complexes with various phosphines and tetrakis(triphenylphosphine) palladium(0). The thiol derivatives (6) can be obtained from the phenolic derivatives (3) via the dialkylthiocarbamate derivatives (4) and (5) according to the general conditions described by M. Newman and H. Karnes, in *J. Org. Chem.*, 1966 31, 3980–4 (1966).

The derivatives of formula I (c) and I (d) can be obtained by oxidizing the derivative I (b), for example using metachloroperbenzoic acid.

When, in the general formula (I), X is an —$NR_9$ radical, the compounds can in this instance be prepared via an Ullman type reaction by direct nucleophilic displacement of a halogenated, preferably iodine-containing, derivative (7) by an aniline derivative (8), in the presence of a base such as potassium dicarbonate or N-methylmorpholine, and of copper:

In the aforesaid formulae and reactions, $R_1$ and $R_2$ are as defined above in respect of the compounds of formula (I) or are derivatives thereof which are suitably protected as to be compatible with the coupling conditions. In particular, when they represent the hydroxyl radical, the latter is preferably protected in the tert-butyldimethylsilyloxy or methoxyethoxymethoxy form. Deprotection is then carried out either in the presence of tetrabutylammonium fluoride or trimethylsilane iodide, or in acidic medium (for example hydrochloric acid).

The present invention also features therapeutic/pharmaceutical applications of the compounds of formula (I).

These compounds exhibit activity in respect of the expression of certain differentiation markers or labels in human keratinocytes in vitro (*Anal. Biochem.*, 192, pp. 232–236, (1991)) and/or exhibit a good comedolytic activity in the Rhino-Mouse test (*Skin Pharmacoloy*, 4, pp. 65–73, (1991)).

The compounds according to the invention are particularly well suited in the following fields of therapy:

(1) for treating dermatological conditions associated with a keratinization disorder related to differentiation and to proliferation, especially for treating acne vulgaris or comedo-type, polymorphic or rosacea acnes, nodulocystic acne or acne conglobata, senile acnes, secondary acnes such as solar acne, acne medicamentosa or occupational acne, (2) for treating other types of keratinization disorders, especially ichthyoses, ichthyosiform states, Darier's disease, keratoses palmaris and plantaris, leucoplakias and leucoplakia-like states, skin or mucosal (buccal) lichen, (3) for treating other dermatological conditions associated with a keratinization disorder manifesting an inflammatory and/or immunoallergic component and, in particular, all of the forms of psoriasis, whether cutaneous, mucous or ungual, and even arthropathic psoriasis, or, alternatively, skin atopy, such as eczema or respiratory atopy or alternatively gingival hypertrophy; the compounds can also be used in certain inflammatory conditions not exhibiting any keratinization disorder, (4) for treating all dermal or epidermal proliferations, whether benign or malignant, whether or not of viral origin, such as verruca vulgaris, verruca plana and epidermodysplasia verruciformis, oral or florid papillomatoses and proliferations which can be induced by ultraviolet radiation, especially in the case of baso- and spinocellular epitheliomas, (5) for treating other dermatological disorders, such as bullous dermatoses and collagen diseases, (6) for treating certain ophthalmological disorders, especially corneopathies, (7) for repairing or combating skin aging, whether photoinduced or chronologic, or to reduce pigmentations and actinic keratoses, or all pathologies associated with chronologic or actinic aging, (8) for preventing or curing the stigmas of epidermal and/or dermal atrophy induced by local or systemic corticosteroids, or any other form of skin atrophy, (9) for preventing or treating cicatrization or healing disorders or for preventing or for repairing vibices,

(10) for combating disorders of the sebaceous function, such as acne hyperseborrhoea or simple seborrhoea,

(11) for the treatment or prevention of cancerous or precancerous states,

(12) for the treatment of inflammatory conditions such as arthritis,

(13) for the treatment of any condition of viral origin at the level of the skin or in general,

(14) for the prevention or treatment of alopecia,

(15) for the treatment of dermatological or general conditions including an immunological component,

(16) for the treatment of conditions of the cardiovascular system, such as arteriosclerosis.

For the aforesaid therapeutic or pharmaceutical applications, compounds according to the invention can advantageously be used in combination with other bioactive compounds displaying retinoid-type activity, with the D vitamins or derivatives thereof, with corticosteroids, with anti-free radical agents, with α-hydroxy or α-keto acids or derivatives thereof, or with ion channel blockers. By "D vitamins or derivatives thereof" are intended, for example, the derivatives of vitamin $D_2$ or $D_3$ and in particular 1,25-dihydroxyvitamin $D_3$. By "anti-free radical agents are intended, for example, α-tocopherol, superoxide dismutase, ubiquinol or certain metal-chelating agents. By "α-hydroxy or α-keto acids or derivatives thereof" are intended, for example, lactic, malic, citric, glycolic, mandelic, tartaric, glyceric or ascorbic acids or salts, amides or esters thereof. By "ion channel blockers" are intended, for example, Minoxidil (2,4-diamino-6-piperidinopyrimidine 3-oxide) and derivatives thereof.

The present invention thus also medicinal features compositions containing at least one compound of formula (I), or one of its chiral or geometric isomers, or one of the salts thereof.

The pharmaceutical/therapeutic compositions of the present invention, intended especially for the treatment of the aforesaid conditions or disease states, comprise a vehicle, carrier or diluent which is pharmaceutically acceptable and compatible with the mode or regime of administration selected for the given composition, at least one compound of formula (I), or one of its chiral or geometric isomers, or one of the salts thereof.

The administration of the compounds according to the invention can be carried out systemically, enterally, parenterally, topically or ocularly.

For enteral administration, the medicinal/pharmaceutical compositions may be in the form of tablets, gelatin capsules, sugar-coated tablets, syrups, suspensions, elixirs, solutions, powders, granules, emulsions, microspheres or nanospheres or lipid or polymeric vesicles which permit a controlled release. For parenteral administration, the compositions may be in the form of solutions or suspensions for perfusion or for injection.

The compounds according to the invention are generally administered at a daily dose of about 0.01 mg/kg to 100 mg/kg of body weight, and this at the rate of 1 to 3 doses per diem.

For topical administration, the pharmaceutical compositions based on compounds according to the invention are more particularly intended for the treatment of the skin and the mucous membranes and can therefore be provided in the form of ointments, creams, milks, pommades, powders, salves, impregnated pads, solutions, gels, sprays, lotions or suspensions. They may also be provided in the form of microspheres or nanospheres or lipid or polymeric vesicles or polymeric patches and hydrogels which permit a controlled release. These compositions for topical administration may, moreover, be provided either in anhydrous form or in an aqueous form according to the particular clinical indication.

For ocular administration, they are principally eye washes.

These compositions for topical or ocular application contain at least one compound of formula (I), or one of its optical or geometric isomers, or alternatively one of its salts, at a concentration preferably ranging from 0.001% to 5% by weight relative to the total weight of the composition.

The compounds of formula (I) according to the invention also find application in the cosmetics field, in particular for body and hair care/hygiene, and especially for the treatment of skins with a tendency to develop acne, for hair regrowth and combating hair loss, for combating the greasy appearance of the skin or the hair, for protecting against the deleterious effects of the sun or in the treatment of physiologically dry skins, for preventing and/or for combating photoinduced or chronologic aging.

For cosmetic applications, the compounds according to the invention may, moreover, be advantageously used in combination with other compounds displaying retinoid-type activity, with the D vitamins or derivatives thereof, with corticosteroids, with anti-free radical agents, with α-hydroxy or α-keto acids or derivatives thereof, or alternatively with ion channel blockers, all these various active agents being as defined above.

The present invention therefore also features cosmetic compositions comprising, in a vehicle, diluent or carrier which is cosmetically acceptable and suitable for a topical application, at least one compound of formula (I), or one of its chiral or geometric isomers, or one of its salts. Such cosmetic compositions are advantageously in the form of a cream, a milk, a lotion, a gel, an ointment, microspheres or nanospheres or lipid or polymeric vesicles, a soap or a shampoo.

The concentration of the compound of formula (I) in the cosmetic compositions according to the invention advantageously ranges from 0.001% to 3% by weight relative to the total weight of the composition.

The medicinal and cosmetic compositions according to the invention may, in addition, contain inert or even pharmacodynamically or cosmetically active additives or combinations of these additives, and especially: wetting agents; depigmenting agents such as hydroquinone, azelaic acid, caffeic acid or kojic acid; emollients; moisturizing or hydrating agents such as glycerol, PEG 400, thiamorpholinone and derivatives thereof or alternatively urea; antiseborrhoeic or antiacne agents such as S-carboxymethylcysteine, S-benzylcysteamine, salts thereof or derivatives thereof, benzoyl peroxide; antibiotics such as erythromycin and esters thereof, neomycin, clindamycin and esters thereof, tetracyclines; antifungal agents such as ketoconazole or 4,5-polymethylene-3-isothiazolidones; agents promoting hair regrowth, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,4-diphenyl-2,4-imidazolidinedione); non-steroidal anti-inflammatory agents; carotenoids and especially β-carotene; anti-psoriatic agents such as anthralin and derivatives thereof; and, lastly, 5,8,11,14-eicosatetraynoic and 5,8,11-eicosatrynoic acids and esters and amides thereof.

The compositions according to the invention may also contain flavor- and taste-enhancing agents, preservatives such as parahydroxybenzoic acid esters, stabilizing agents, moisture regulating agents, pH regulating agents, osmotic pressure modifying agents, emulsifying agents, UV-A and UV-B screening agents, and antioxidants such as α-tocopherol, butylated hydroxyanisole or butylated hydroxytoluene.

In order to further illustrate the present iinvention and the advantages thereof, the following specific examples are given, it being understood that same are intended only as illustrative and in nowise limitative.

EXAMPLE 1

Preparation of 4-(5,6,7,8-tetrahydro-5,5,8,8-tetramethyl-2-naphthyloxy)benzoic acid:

(a) Synthesis of methyl 4-(5,6,7,8-tetrahydro-5,5,8,8-tetramethyl-2-naphthyloxy)benzoate:

5.3 g (15 mmol) of 5,6,7,8-tetrahydro-5,5,8,8-tetramethyl-2-naphthol and 70 ml of pyridine were introduced into a three-necked flask under a nitrogen stream, and 430 mg (15 mmol) of sodium hydride (80% in oil) were added in small amounts. The mixture was stirred for 30 minutes, 3.9 g (15 mmol) of methyl 4-iodobenzoate and 4.6 g (22.5 mmol) of a copper bromide and dimethyl sulfide complex were added successively and the resulting mixture was heated at reflux for 16 hours. The reaction medium was evaporated to dryness, taken up in water and ethyl ether, the organic phase decanted off, dried over magnesium sulfate and evaporated.

The residue obtained was purified by chromatography on a silica column eluted with dichloromethane and hexane (50/50). After evaporation of the solvents, 3.4 g (67%) of the expected methyl ester were recovered.

(b) Synthesis 4-(5,6,7,8-tetrahydro-5,5,8,8-tetramethyl-2-naphthyloxy)benzoic acid:

3.4 g (10 mmol) of the ester obtained in step (a), 40 ml of THF and 40 ml of a methanolic sodium hydroxide solution (2N) were introduced into a round-bottomed flask and the entire contents were stirred at room temperature for 8 hours. The reaction medium was evaporated to dryness, taken up in water, acidified to pH 1, extracted with ethyl ether, the organic phase decanted off, dried over magnesium sulfate and evaporated.

The residue obtained was purified by chromatography on a silica column eluted with a mixture of dichloromethane and ethyl ether (97/3). After evaporation of the solvents, 2.3 g (71%) of the expected acid of melting point 234–5° C. were recovered.

EXAMPLE 2

Preparation of 4-(5,6,7,8-tetrahydro-5,5,8,8-tetrainethyl-2-naphthylthio)benzoic acid:

(a) Synthesis of ethyl 4-(5,6,7,8-tetrahydro-5,5,8,8-tetramethyl-2-naphthylthio)benzoate:

30 ml of ethyl alcohol were introduced into a round-bottomed flask, then 500 mg (23 mmol) of sodium were added in small amounts and the entire contents were stirred for 30 minutes. Next, 2 g (9.1 mmol) of 5,6,7,8-tetrahydro-5,5,8,8-tetramethyl-2-naphthylthiol, 2.4 g (9.1 mmol) of methyl 4-iodobenzoate and 100 mg (0.09 mmol) of tetrakis(triphenylphosphine)palladium(0) were added successively, and then the reaction mass was heated at reflux for four hours. The reaction medium was evaporated, taken up in water and ethyl acetate, the organic phase decanted off, washed with water, dried over magnesium sulfate and evaporated.

The residue obtained was purified by chromatography on a silica column eluted with dichloromethane. After evaporation of the solvents, 2.1 g (63%) of ethyl ester were recovered.

(b) Synthesis of 4-(5,6.7,8-tetrahydro-5,5,8,8-tetramethyl-2-naihthylthio)benzoic acid:

In a manner similar to Example 1 (b) above, starting with 1.9 g (5.2 mmol) of the ethyl ester obtained in step (a), 1.6 g (90%) of the expected acid of melting point 187–8° C. were obtained.

EXAMPLE 3

Preparation of 4-(5,6,7,8-tetrahydro-5,5,8,8-tetramethyl-2-naphthylsulfinyl)benzoic acid:

(a) Synthesis of ethyl 4-(5,6,7,8-tetrahydro-5 5,8,8-tetramethyl-2-naphthylsulfinyl)benzoate:

1.1 g (3.1 mmol) of ethyl 4-(5,6,7,8-tetrahydro-5,5,8,8-tetramethyl-2-naphthylthio)benzoate and 30 ml of dichloromethane were introduced into a round-bottomed flask, and 970 mg (3.1 mmol) of meta-chloroperbenzoic acid were then added. The entire contents were stirred at room temperature for two hours, the reaction medium poured into water, extracted with dichloromethane, the organic phase decanted off, dried over magnesium sulfate and evaporated. The residue was purified by chromatography on a silica column eluted with dichloromethane. After evaporation of the solvents, 1 g (84%) of the expected ester was recovered.

(b) Synthesis of 4-(5,6,7,8-tetrahydro-5,5,8,8-tetramethyl-2-naphthylsulfinyl)benzoic acid:

In a manner similar to Example 1 (b) above, starting with 960 mg (2.5 mmol) of the ethyl ester obtained in step (a), 890 mg (99%) of the expected acid of melting point 214–60° C. were obtained.

EXAMPLE 4

Preparation of 4-(5,6,7,8-tetrahydro-5,5,8,8-tetramethyl-2-naphthylsulfonyl)benzoic acid:

(a) Synthesis of ethyl 4-(5,6,7,8-tetrahydro-5,5,8,8-tetramethyl-2-naphthylsulfonyl)benzoate:

1.05 9 (2.8 mmol) of ethyl 4-(5,6,7,8-tetrahydro-5,5,8,8-tetramethyl-2-naphthylthio)benzoate and 30 ml of dichloromethane were introduced into a round-bottomed flask, and 2.45 g (7.12 mmol) of meta-chloroperbenzoic acid were then added. The entire contents were stirred at room temperature for two hours, the reaction medium poured into water, extracted with dichloromethane, the organic phase decanted off, dried over magnesium sulfate and evaporated.

The residue was purified by chromatography on a silica column eluted with dichloromethane. After evaporation of the solvents, 1.09 g (95 %) of the expected ester was recovered.

(b) Synthesis of 4-(5,6,7,8-tetrahydro-5,5,8,8-tetramethyl-2-naphthylsulfonyl)benzoic acid:

In a manner similar to Example 1 (b) above, starting with 1.09 g (2.7 mmol) of the ethyl ester obtained in step (a), 1 g (99 %) of the expected acid of melting point 218–20° C. was obtained.

EXAMPLE 5

Preparation of 4-(5,6,7,8-tetrahydro-5,5,8,8-tetramethyl -2-naphthylamino)benzoic acid:

1.02 g (5 mmol) of 5,6,7,8-tetrahydro-5,5,8,8-tetramethyl-2-naphthylamine, 1.24 g (5 mmol) of 4-iodobenzoic acid, 820 µl (7.5 mmol) of N-methylmorpholine, 360 mg (2.5 mmol) of $Cu_2O$ and 15 ml of dioxane were introduced successively into a round-bottomed flask. The entire contents were heated at reflux for 24 hours, the reaction medium poured into 15 ml of 5N hydrochloric acid, the precipitate filtered and the latter washed with water.

The solids were triturated in ethyl alcohol, filtered and dried. 200 mg (12 %) of the expected acid of melting point 262–4° C. were then recovered.

EXAMPLE 6

Preparation of 5-(5,6,7,8-tetrahydro-5,5,8,8-tetramethyl-2-naphthylthio)-2-thiophenecarboxylic acid:

40 ml of n-butyl alcohol were introduced into a round-bottomed flask and then 300 mg (13 mmol) of sodium were added in small amounts and the entire contents were stirred for thirty minutes. Next, 1.1 g (5 mmol) of 5,6,7,8-tetrahydro-5,5,8,8-tetramethyl-2-naphthylthiol, 1.1 g (5 mmol) of methyl 5-bromo-2-thiophenecarboxylate and 230 mg (0.2 mmol) of tetrakis(triphenylphosphine)palladium(0) were added successively and then the reaction mass was heated at reflux for four hours. The reaction medium was evaporated, taken up in water and ethyl acetate, the organic phase decanted off, washed with water, dried over magnesium sulfate and evaporated.

The residue obtained was purified by chromatography on a silica column eluted with ethyl acetate and hexane (60/40). After evaporation of the solvents, 180 mg (10 %) of 5-(5,6,7,8-tetrahydro-5,5,8,8-tetramethyl-2-naphthylthio)-2-thiophenecarboxylic acid of melting point 141–20° C. were recovered.

EXAMPLE 7

Preparation of 4-(3,5,5,8,8-pentamethyl-5,6,7,8-tetrahydro-2-nayhthyloxy)benzoic acid:

(a) Synthesis of 3,5,5,8,8--entamethyl-5, 6,7.8-tetrahydro-2-naphthol:

50.8 g (0.27 mol) of 2,5-dichloro-2,5-dimethylhexane, 30 g (0.27 mol) of 2-methylphenol and 500 ml of dichloromethane were introduced into a three-necked flask. 14.8 g (0.11 mol) of aluminum chloride were added in small amounts at 0° C. and the entire contents were stirred at room temperature for twelve hours. The reaction medium was poured into ice-cold water, extracted with dichloromethane, the organic phase decanted off, washed with sodium bicarbonate, dried over magnesium sulfate and evaporated.

The residue obtained was triturated in hexane, filtered and 54.4 g (90%) of the expected phenol of melting point 125–6° C. were then recovered after drying.

(b) Synthesis of methyl 4-(3,5,5,8,8-pentamethyl-5,6,7,8-tetrahydro-2-naphthyloxy)benzoate:

In a manner similar to Example 1 (a) above, by the reaction of 1.1 g (5 mmol) of 3,5,5,8,8-pentamethyl-5,6,7,8-tetrahydro-2-naphthol with 0.89 g (4.1 mmol) of methyl 4-bromobenzoate, 670 mg (46%) of the expected methyl ester of melting point 133–5° C. were obtained.

(c) Synthesis of 4-(3.5,5,8,8-pentamethyl-5,6,7,8-tetrahydro-2-naphthyloxy)benzoic acid:

In a manner similar to Example 1(b) above, starting with 670 mg (1.9 mmol) of the methyl ester obtained in step (b), 620 mg (96%) of the expected acid of melting point 208–10° C. were obtained.

EXAMPLE 8

Preparation of 4-(3,5,5,8,8-pentamethyl-5,6,7,8-tetrahydro-2-naphthylthio)benzoic acid:

(a) Synthesis of 0-3,5,5,8,8-pentamethyl-5.6,7,8-tetrahydro-2-naphthyldimethylthiocarbamate:

4.1 g (0.138 mol) of sodium hydride (80% in oil) and 200 ml of DMF were introduced into a round-bottomed flask and under a nitrogen stream. The mixture was cooled to 0° C. and a solution of 25.2 g (0.115 mol) of 3,5,5,8,8-pentamethyl-5,6,7,8-tetrahydro-2-naphthol in 100 ml of DMF was added dropwise and the entire contents were stirred until the evolution of gas ceased. Next, a solution of 18.55 g (0.15 mol) of dimethylthiocarbamoyl chloride in 200 ml of DMF was added and the reaction mass was again stirred for eight hours at room temperature. The reaction medium was then poured into water, extracted with ethyl acetate, the organic phase decanted off, washed with water, dried over magnesium sulfate and finally evaporated.

The solids obtained were purified by chromatography on a silica column eluted with a mixture of ethyl acetate and hexane (30/70). After evaporation of the solvents, 20 g (68%) of the expected compound of melting point 110–10° C. were recovered.

(b) Synthesis of S-3,5,5,8,8-pentamethyl-5,6,7,8-tetrahydro-2-naphthyldimethylthiocarbamate:

20.1 g (65.8 mmol) of the compound obtained in step (a) were introduced into a round-bottomed flask under a nitrogen stream and the mixture was heated at 240° C. for six hours. The reaction medium was extracted with dichloromethane, washed with water, the organic phase decanted off, dried over magnesium sulfate and evaporated. 18.1 g (90%) of the expected compound of melting point 138–9° C. were recovered.

(c) Synthesis of 3,.5,5,8,8-pentamethyl-5,6,7,8-tetrahydro-2-naphthylthiol:

23 g (75 mmol) of the compound obtained in step (b) and 300 ml of methyl alcohol were introduced into a round-bottomed flask. 30 g (75 mmol) of sodium hydroxide were added and the entire contents were heated at reflux for three hours. The reaction medium was evaporated, taken up in water, acidified with concentrated hydrochloric acid and finally filtered.

The solid obtained were washed with water, dried, and 18 9 (99%) of 3,5,5,8,8-pentamethyl-5,6,7,8-tetrahydro-2-naphthylthiol of melting point 97-8° C. were then recovered.

(d) Synthesis of ethyl 4-(3,5,5,8,8-pentamethyl-5,6,7,8-tetrahydro-2-naphthylthiozbenzoate:

In a manner similar to Example 2 (a) above, by the reaction of 2 g (8.5 mmol) of 3,5,5,8,8-pentamethyl-5,6,7,8-tetrahydro-2-naphthylthiol with 2.24 g (8.5 mmol) of methyl 4-iodobenzoate, 2 g (63%) of ethyl ester of melting point 109–10° C. were obtained after recrystallization from ethyl alcohol.

(e) Synthesis of 4-(3,5,5,8,8-pentamethyl-5,6,7,8-tetrahydro-2-naphthylthio)benzoic acid:

In a manner similar to Example 1 (b) above, starting with 2 g (5.2 mmol) of the ethyl ester obtained in step (d), 1.58 g (85%) of the expected acid of melting point 253–4° C. was obtained.

EXAMPLE 9

Preparation of 4-(3-ethyl-5,5,8,8-tetramethyl-5,6,7,8-tetrahydro-2-naphthyloxy)benzoic acid:

(a) 3-ethyl-5,5,8,8-tetramethyl-5,6,7,8-tetrahydro-2-naphthol

In a manner similar to Example 7 (a) above, by the reaction of 15 g (0.123 mol) of 2-ethylphenol with 22.5 g (0.123 mol) of 2,5-dichloro-2,5-dimethylhexane, 25.4 g (89%) of the expected phenol of melting point 88–9° C. were obtained after chromatography on a silica column eluted with dichioromethane.

(b) Synthesis of methyl 4-(3-ethyl-5,5,8,8-tetramethyl-5,6,7,8-tetrahydro-2-naphthyloxy)benzoate:

In a manner similar to Example 1 (a) above, by the reaction of 2 g (8.6 mmol) of 3-ethyl-5,5,8,8-tetramethyl-5, 6,7,8-tetrahydro-2-naphthol with 1.52 g (7 mmol) of methyl 4-bromobenzoate, 1.5 g (56%) of the expected methyl ester was obtained in the form of a yellow oil.

(c) Synthesis of 4-(3-ethyl-5,5,8,8-tetramethyl-5,6.7.8-tetrahydro-2-naihthyloxy)benzoic acid:

In a manner similar to Example 1 (b) above, starting with 1.5 g (4 mmol) of the methyl ester obtained in step (b), 1.24 g (86%) of the expected acid of melting point 195–6° C. was obtained.

EXAMPLE 10

Preparation of 4- (3-isopropyl-5,5,8,8-tetramethyl-5, 6,7,8-tetrahydro-2-naphthyloxy)benzoic acid:

(a) 3-isopropyl-5,5,8,8-tetramethyl-5,6,7,8-tetrahydro-2-naphthol

In a manner similar to Example 7(a) above, by the reaction of 30 g (0.22 mol) of 2-isopropylphenol with 40.3 g (0.22 mol) of 2,5-dichloro-2,5-dimethylhexane, 48.9 g (90%) of the expected phenol of melting point 79–80° C. were obtained after chromatography on a silica column eluted with a mixture of dichloromethane and hexane (40/60).

(b) Synthesis of methyl 4-(3-isoproyl-5,5,8,8-tetramethyl-5,6,7,8-tetrahydro-2-naphthyloxy)benzoate:

In a manner similar to Example 1(a) above, by the reaction of 2 g (8.1 mmol) of 3-isopropyl-5,5,8,8-tetramethyl-5,6,7,8-tetrahydro-2-naphthol with 1.45 g (6.7 mmol) of methyl 4-bromobenzoate, 840 mg (33%) of the expected methyl ester of melting point 115–6° C. were obtained.

(c) Synthesis of 4-(3-isoproyol-5,5,8,8-tatramethyl-5,6,7,8-tetrahydro-2-naphthyloxy)benzoic acid:

In a manner similar to Example 1(b) above, starting with 800 mg (2.1 mmol) of the methyl ester obtained in step (b), 690 mg (90%) of the expected acid of melting point 205–6° C. were obtained.

EXAMPLE 11

Preparation of 4-(5,6,7,8-tetrahydro-5,5,8,8-tetramethyl-2-naphthyloxy)acetophenone:

In a manner similar to Example 1 (a) above, by the reaction of 6.6 g (32 mmol) of 5,6,7,8-tetrahydro-5,5,8,8-tetramethyl-2-naphthol with 5.4 g (27 mmol) of 4-bromoacetophenone, 6.3 g (72%) of the expected ketone were obtained in the form of a slightly yellow oil.

EXAMPLE 12

Preparation of 4-(5,6,7,8-tetrahydro-5.5,8,8-tetramethyl-2-naphthyloxy)benzaldehyde:

In a manner similar to Example 1 (a) above, by the reaction of 5.3 g (15 mmol) of 5,6,7,8-tetrahydro-5,5,8,8-tetramethyl-2-naphthol with 3.1 g (16.5 mmol) of 4-bromobenzaldehyde, 2.4 g of the expected aldehyde of melting point 75–60° C. were obtained after purification by chromatography on a silica column eluted with a mixture of dichloromethane and hexane (50/50).

EXAMPLE 13

Preparation of 4-(3-bromo-5,6,7,8-tetrahydro-5,5,8, 8-tetramethyl-2-naphthyloxy)benzoic acid:

(a) Synthesis of methyl 4-(3-bromo-5,6,7,8-tetrahydro-5, 5,8, 8-tetramethyl-2-naphthyloxy)benzoate:

In the manner similar to Example 1 (a), by the reaction of 1 g (3.5 mmol) of 3-bromo-5,6,7,8-tetrahydro-5,5,8,8-tetramethyl-2-naphthol with 770 mg (2.94 mmol) of methyl 4-iodobenzoate, 700 mg (58%) of obtained.

(b) Synthesis of 4-(3-bromo-5,6,7,8-tetrahydro-5,5,8,8-tetramethyl-2-naphthyloxy)benzoic acid:

In a manner similar to Example 1(b), starting with 700 mg (1.6 mmol) of the preceding methyl ester, 650 mg (95%) of 4-(3-bromo-5,6,7,8-tetrahydro-5,5,8,8-tetramethyl-2-naphthyloxy)benzoic acid of melting point 229–30° C. were obtained.

EXAMPLE 14

Preparation of 3-methyl-4-(5,6,7,8-tetrahydro-5,5,8, 8-tetramethyl-2-naphthylthio)benzoic acid:

(a) Synthesis of 3-methyl-4-iodobenzoic acid:

20 g (0.132 mol) of 3-methyl-4-aminobenzoic acid and 175 ml of sulfuric acid (20%) were introduced into a three-necked flask. A solution of 11.9 g (0.172 mol) of sodium nitrite in 50 ml of water was added dropwise at −10° C. and the mixture was stirred for 2 hours. This solution was introduced dropwise, via a funnel cooled at −50° C., into a solution of 35 g (0.211 mol) of potassium iodide, 35.2 g (0.185 mol) of copper iodide and 175 ml of sulfuric acid (20%). The mixture was stirred for 8 hours, the reaction medium filtered, the solid obtained dissolved in ethyl acetate, washed with water and then with a solution of sodium sulfite, dried over magnesium sulfate and evaporated. 24.4 g (70%) of 3-methyl-4-iodobenzoic acid of melting point 205–10° C. were recovered.

(b) Synthesis of methyl 3-methyl-4-iodobenzoate:

24.4 g (0.093 mol) of 3-methyl-4-iodobenzoic acid and 250 ml of methanol were introduced into a round-bottomed flask and 2.5 ml of concentrated sulfuric acid were added dropwise. The mixture was heated. at reflux for 12 hours, the reaction medium evaporated, taken up in ethyl acetate and water, the organic phase decanted off, dried over magnesium sulfate and evaporated. The residue was triturated in methanol, filtered and 21.9 g (85%) of the expected methyl ester of melting point 58–9° C. were recovered.

(c) Synthesis of 3-methyl-4-(5,6,7,8-tetrahydro-5,5,8,8-tetramethyl-2-naphthylthio)benzoic acid:

In a manner similar to Example 2(a), by the reaction of 2.4 g (11 mmol) of 5,6,7,8-tetrahydro-5,5,8,8-tetramethyl-2-naphthylthiol with 3 g (11 mmol) of methyl 3-methyl-4-iodobenzoate, 1.96 g (51%) of 3-methyl-4-(5,6,7,8-tetrahydro-5,5,8,8-tetramethyl-2-15 naphthylthio)benzoic acid of melting point 195–6° C. was directly obtained.

EXAMPLE 15

Preparation of 3-methyl-4-(3,5,5,8,8-pentamethyl-5,6,7, 8-tetrahydro-2-naphthylthio)benzoic acid:

(a) Synthesis of methyl 3-methyl-4-(3,5,5,8,8-pentamethyl-5,6,7,8-tetrahydro-2-naphthylthio)benzoate:

In a manner similar to Example 2(a), by the reaction of 2.55 g (11 mmol) of 3,5,5,8,8-pentamethyl-5,6,7,8-tetrahydro-2-naphthylthiol with 3 g (11 mmol) of methyl 3-methyl-4-iodobenzoate, 1.86 g (43%) of the expected compound in the form of an ethyl ester was obtained as an orange-colored oil.

(b) Synthesis of 3-methyl-4-(3,5,5,8,8-pentamethyl-5,6,7, 8-tetrahydro-2-naphthylthio)benzoic acid:

In a manner similar to Example 1 (b), starting with 1.86 g (4.7 mmol) of the preceding ethyl ester, 1.5 g (97%) of 3-methyl-4-(3,5,5,8,8-pentamethyl-5,6,7,8-tetrahydro-2-naphthylthio)benzoic acid of melting point 217–8° C. was obtained.

EXAMPLE 16

Preparation of 3-methyl-4-(3-ethyl-5,6,7,8-tetrahydro-5,5,8,8-tetramethyl-2-naphthyloxy)benzoic acid:

(a) Synthesis of methyl 3-methyl-4-(3-ethyl-5,6,7,8-tetrahydro-5,5,8,8-tetramethyl-2-naphthyloxy)benzoate:

In a manner similar to Example 1(a), by the reaction of 2.1 g (8.7 mmol) of 3-ethyl-5,6,7,8-tetrahydro-5,5,8,8-tetramethyl-2-naphthol with 2 g (7.2 mmol) of methyl 3-methyl-4-iodobenzoate, 2.18 g (79%) of the expected methyl ester was obtained in the form of a pale yellow oil.

(c) Synthesis of 3-methyl-4-(3-ethyl-5,6,7,8-tetrahydro-5,5S,8,8-tetramethyl-2-naphthyloxy)benzoic acid:

In a manner similar to Example 1 (b), starting with 2.18 g (5.7 mmol) of the preceding methyl ester, 1.9 g (90%) of 3-methyl-4-(3-ethyl-5,6,7,8-tetrahydro-5,5,8,8-tetramethyl-2-naphthyloxy)benzoic acid of melting point 210–1° C. were obtained.

EXAMPLE 17

Preparation of 6-(3,5,5,8,8-pentamethyl-5,6,7,8:tetrahydro-2-naphthylthio)nicotinic acid:

(a) Synthesis of ethyl 6-(3,5,5,8.8-pentamethyl-5,6,7,8-tetrahydro-2-naphthylthio)nicotinate:

In a manner similar to Example 2(a), by the reaction of 800 mg (3.4 mmol) of 3,5,5,8,8-pentamethyl-5,6,7,8-tetrahydro-2-naphthylthiol with 900 mg (3.4 mmol) of methyl 6-iodonicotinate, 620 mg (47%) of the expected compound were obtained in the form of an ethyl ester.

(b) Synthesis of 6-(3,5,5,8,8-pentamethyl-5,6,7,8-tetrahydro-2-naphthylthio)nicotinic acid:

In a manner similar to Example 1 (b), starting with 620 mg (1.6 mmol) of the preceding ethyl ester, 520 mg (90%) of 6-(3,5,5,8,8-pentamethyl-5,6,7,8-tetrahydro-2-naphthylthio)nicotinic acid of melting point 257–60° C. were obtained.

EXAMPLE 18

Preparation of 2-hrdroxy-4-(3,5,5,8,8-pentamethyl-5,6,7,8-tetrahydro-2-naphthylthio)benzoic acid:

(a) Synthesis of ethyl 2-hydroxy-4-(3,5,5,8,8-pentamethyl-5,6,7,8-tetrahydro-2-naphthylthio)benzoate:

In a manner similar to Example 2(a), by the reaction of 2 g (8.53 mmol) of 3,5,5,8,8-pentamethyl-5,6,7,8-tetrahydro-2-naphthylthiol with 2.37 g (8.53 mmol) of methyl 2-hydroxy-4-iodobenzoate, 2.42 g (71%) of the expected compound were obtained in the form of an ethyl ester of melting point 74–5° C.

(b) Synthesis of 2-hydroxy-4-(3,5,5,8,8-pentamethyl-5,6,7,8-tetrahydro-2-nanhthylthio)benzoic acid:

In a manner similar to Example 1 (b), starting with 2.4 g (6.1 mmol) of the preceding ethyl ester, 2.06 g (92%) of 2-hydroxy-4-(3,5,5,8,8-pentamethyl-5,6,7,8-tetrahydro-2-naphthylthio)benzoic acid of melting point 197–200° C. were obtained.

EXAMPLE 19

Preparation of 2-chloro-4-(3,5,5,8,8-pentamethyl-5,6,7,8-tetrahydro-2-naphthylthio)benzoic acid:

(a) Synthesis of 2-chloro-4-iodobenzoic acid:

In a manner similar to Example 14(a), starting with 10 g (58.3 mmol) of 2-chloro-4-aminobenzoic acid, 14.26 g (86%) of 2-chloro-4-iodobenzoic acid were recovered.

(b) Synthesis of methyl 2-chloro-4-iodobenzoate:

In a manner similar to Example 14(b), starting with 13.9 g (49.2 mmol) of 2-chloro-4-iodobenzoic acid, 11.52 g (79%) of the expected methyl ester were obtained in the form of an oil.

(c) Synthesis of ethyl 2-chloro-4-(3,5,5,8,8-pentamethyl-5,6,7,8-tetrahydro-2-naphthylthio)benzoate:

In a manner similar to Example 2(a), by the reaction of 2 g (8.5 mmol) of 3,5,5,8,8-pentamethyl-5,6,7,8-tetrahydro-2-naphthylthiol with 2.41 g (8.5 mmol) of methyl 2-chloro-4-iodobenzoate, 1.25 9 (35%) of the expected compound was obtained in the form of an ethyl ester.

(d) Synthesis of 2-chloro-4-(3,5,5,8,8-pentamethyl-5,6,7,8-tetrahydro-2-naphthylthio)benzoic acid:

In a manner similar to Example 1 (b), starting with 1.25 g (3 mmol) of the preceding ethyl ester, 1 g (96%) of 2-chloro-4-(3,5,5,8,8-pentamethyl-5,6,7,8-tetrahydro-2-naphthylthio)benzoic acid of melting point 202–5° C. was obtained.

EXAMPLE 20

Preparation of 4-(3-ethyl-5,6,7,8-tetrahydro-5,5,8,8-tetramethyl-2-naphthylthio)benzoic acid:

(a) Synthesis of 0–3-ethyl-5,6,7,8-tetrahydro-5,5,8,8-tetramethyl-2-narhthyldimethyl-thiocarbamate:

In a manner similar to Example 8 (a), by the reaction of 5 g (21 mmol) of 3-ethyl-5,6,7,8-tetrahydro-5,5,8,8-tetramethyl-2-naphthol with 3.5 g (2.8 mmol) of dimethylthiocarbamoyl chloride, 4.9 g (72%) of the expected compound of melting point 82–3° C. were obtained.

(b) Syntheiss of S-3-ethyl-5,6,7,8-tetrahydro-5,5,8,8-tetramethyl-2-naphthyldimethyl-thiocarbamate:

In a manner similar to Example 8 (b), starting with 4.5 g (14 mmol) of the preceding product, 4.5 g (99%) of S-3-ethyl-5,6,7,8-tetrahydro-5,5,8,8-tetramethyl-2-naphthyldimethylthiocarbamate were obtained in the form of a chestnut-colored oil.

(c) Synthesis of 3-ethyl-5,6,7,8-tetrahydro-5,5,8,8-tetramethrl-2-naphthylthiol:

In a manner similar to Example 8(c), starting with 4.5 g (14 mmol) of the preceding product, 2.9 g (84%) of the expected thiol were obtained in the form of an orange-colored oil.

(d) Synthesis of ethyl 4-(3-ethyl-5,6,7,8-tetrahydro-5,5,8,8-tetramethyl-2-naphthylthio)benzoate:

In a manner similar to Example 2(a), by the reaction of 2 g (8.5 mmol) of 3-ethyl-5,6,7,8-tetrahydro-5,5,8,8-tetramethyl-2-naphthylthiol with 2.1 g (8 mmol) of methyl 4-iodobenzoate, 1.9 g (64%) of the expected compound was obtained in the form of an ethyl ester.

(e) Synthesis of 4-(3-ethyl-5,6,7,8-tetrahydro-5,5,8,8-tetramethyl-2-naphthylthio)benzoic acid:

In a manner similar to Example 1 (b), starting with 1.9 g (5.1 mmol) of the preceding ethyl ester, 1.7 g (89%) of 4-(3-ethyl-5,6,7,8-tetrahydro-5,5,8,8-tetramethyl-2-naphthylthio)benzoic acid of melting point 232–5° C. was obtained.

EXAMPLE 21

Preparation of ethyl 4-(3-isopropyl-5,6,7,8-tetrahydro-5,5,8,8-tetramethyl-2-nayhthylthio) benzoate:

(a) Synthesis of 0-3-isopro-yl-5,6,7,8-tetrahydro-5,5,8,8-tetramethyl-2-naphthyldimethyl-thiocarbamate:

In a manner similar to Example 8(a), by the reaction of 5 g (20.3 mmol) of 3-isopropyl-5,6,7,8-tetrahydro-5,5,8,8-tetramethyl-2-naphthol with 3.26 g (26.4 mmol) of dimethylthiocarbamoyl chloride, 2.26 9 (33%) of the expected compound of melting point 99–100° C. were obtained.

(b) Synthesis of S-3-isopro-yl-5,6,7,8-tetrahydro-5,5,8,8-tetramethyl-2-naphthyldimethyl-thiocarbamate:

In a manner similar to Example 8(b), starting with 2.9 g (8.7 mmol) of the preceding product, 1.63 g (56%) of S-3-ethyl-5,6,7,8-tetrahydro-5,5,8,8-tetramethyl-2-naphthyldimethylthiocarbamate of melting point 103–4° C. was obtained.

(c) Synthesis of 3-isopropyl-5,6,7,8-tetrahydro-5,5,8,8-tetramethyl-2-naphthylthiol:

In a manner similar to Example 8(c), starting with 4.5 g (14 mmol) of the preceding product, 2.9 g (84%) of the expected thiol were obtained in the form of an orange-colored oil.

(d) Synthesis of ethyl 4-(3-isopropyl-5,6,7,8-tetrahydro-5,5,8,8-tetramethyl-2-naphthylthio)benzoate:

In a manner similar to Example 2(a), by the reaction of 1.35 g (5.1 mmol) of 3-isopropyl-5,6,7/8-tetrahydro-5,5,8,8-tetramethyl-2-naphthylthiol with 1.1 g (5.1 mmol) of methyl 4-bromobenzoate, 1.3 g (66%) of the expected compound was obtained in the form of an ethyl ester.

EXAMPLE 22

Preparation of ethyl 4-(3-n-prop-1-5,6,7,8-tetrahydro-5,5,8,8-tetramethyl-2-naphthylthio) benzoate:

(a) Synthesis of 3-n-Pro-yl-5,6,7.8-tetrahydro-5,5,8,8-tetramethyl-2-naphthol:

In a manner similar to Example 7(a), by the reaction of 13.6 g (0.1 mol) of 2-n-propylphenol with 18.3 g (0.1 mol) of 2,5-dichloro-2,5-dimethylhexane, 11.6 g (65%) of the expected phenolic derivative of melting point 96–7° C. were obtained after chromatography on a silica column eluted with dichloromethane.

(b) Synthesis of 0-3-n-propyl-5,6,7,8-tetrahydro-5,5,8,8-tetramethyl-2-naphthyldimethyl-thiocarbamate:

In a manner similar to Example 8(a), by the reaction of 15 g (61 mmol) of 3-propyl-5,6,7,8-tetrahydro-5,5,8,8-tetramethyl-2-naphthol with 9.8 9 (79 mmol) of dimethylthiocarbamoyl chloride, 15.9.g (78%) of O-3-n-propyl-5,6,7,8-tetrahydro-5,5, 8,8-tetramethyl-2-naphthyldimethylthiocarbamate were obtained.

(c) Synthesis of S-3-n-pro-yl-5,6,7,8-tetrahydro-5,5,8,8-tetramethyl-2-naphthyldimethyl-thiocarbamate:

In a manner similar to Example 8(b), starting with 10 g (30 mmol) of the preceding product, 6.8 g (68%) of S-3-n-propyl-5,6,7,8-tetrahydro-5,5,8,8-tetramethyl-2-naphthyldimethylthiocarbamate of melting point 102–4° C. were obtained.

(d) Synthesis of 3-n--roT)1-5,6,7,8-tetrahydro-5,5,8,8-tetramethyl-2-naphthylthiol:

In a manner similar to Example 8(c), starting with 6.8 g (20.4 mmol) of the preceding product, 5 g (93%) of the expected thiol were obtained in the form of a colorless oil.

(e) Synthesis of ethyl 4-(3-n-propyl -5,6,7.8-tetrahydro-5,5,8,8-tetramethyl-2-naphthylthio)benzoate:

In a manner similar to Example 2(a), by the reaction of 2 g (7.6 mmol) of 3-n-propyl-5,6,7,8-tetrahydro-5,5,8,8-tetramethyl-2-naphthylthiol with 2 g (7.6 mmol) of methyl 4-iodobenzoate, 2 g (65%) of the expected compound were obtained in the form of an ethyl ester.

EXAMPLE 23

Preparation of 4-(3,5,5,8,8-pentamethyl-5,6,7,8-tetrahydro-2-naphthylthio)benzenemethanol:

144 mg (3.8 mmol) of lithium aluminum hydride and 50 ml of THF were introduced into a three-necked flask and under a nitrogen stream. Next, a solution of 1.4 g (3.8 mmol) of ethyl 4-(3,5,5,8,8-pentamethyl-5,6,7,8-tetrahydro-2-naphthylthio)benzoate in 25 ml of THF was introduced dropwise and the mixture was heated at reflux for 8 hours. The excess hydride was destroyed with a potassium sodium tartrate solution and the reaction medium was extracted with ethyl acetate. The organic phase was decanted off, dried over magnesium sulfate and evaporated.

The residue obtained is purified by chromatography on a silica column eluted with a mixture of heptane and ethyl acetate (90/10). 660 mg (51%) of the expected alcohol of melting point 81–2° C. were recovered.

EXAMPLE 24

Preparation of 4-(3,5,5,8,8-pentamethyl-5,6,7,8-tetrahydro-2 -naphthylthio) benzaldehyde:

60 µl (0.7 mmol) of oxalyl chloride and 5 ml of dichloromethane were introduced into a three-necked flask and under a nitrogen stream. 100 Al (1.4 mmol) of DMSO were added at –60° C. and the mixture was stirred for 10 min and then a solution of 200 mg (0.6 mmol) of 4-(3,5,5,8,8-pentamethyl-5,6,7,8-tetrahydro-2-naphthylthio) benzenemethanol in 5 ml of dichloromethane and 400 µl (3 mmol) of triethylamine was added. The mixture was stirred at room temperature for one hour, the reaction medium poured into water, extracted with dichloromethane, the organic phase decanted off, dried over magnesium sulfate and evaporated.

The residue obtained was purified by chromatography on a silica column eluted with a mixture of heptane and ethyl acetate (80/20). 145 mg (73%) of the expected aldehyde of melting point 98–9° C. were recovered.

EXAMPLE 25

Preparation of N-ethyl-4-(3,5,5,8,8-pentamethyl-5,6, 7,8-tetrahydro -2-naphthylthio) benzarnide:

(a) Synthesis of 4-(3,5,5,8,8-pentamethyl-5,5,6,7,8-tetrah-vdro-2-naphthylthio)benzoyl chloride:

A solution of 1.4 g (4 mmol) of 4 -(3, 5,5, 8, 8-pentamethyl -5,6,7,8 -tetrahydro-2 -naphthylthio) benzoic acid in 100 ml of anhydrous dichloromethane was introduced into a round-bottomed flask, 900 µl (4.4 mmol) of dicyclohexylamine were added and the mixture was stirred for one hour. Next, 320 µl mixture was stirred for one hour.

The reaction medium was evaporated to dryness, taken up in anhydrous ethyl ether, the dicyclohexylamine salt filtered off and the filtrate evaporated. 1.5 g (100%) of the crude acid chloride was recovered which was used as such in the continuation of the synthesis to follow.

(b) Synthesis of N-ethyl-4-(3,5,5,8,8-pentamethyl-5,6,7,8-tetrahydro-2-naphthylthio)benzamide:

640 Al (8 mmol) of a 70% solution of ethylamine and 20 ml of THF were introduced into a round-bottomed flask. A solution of 735 mg (2 mmol) of 4-(3,5,5,8,8-pentamethyl-5,6,7,8-tetrahydro-2-naphthylthio)benzoyl chloride dissolved in 30 ml of THF was added dropwise and the mixture was stirred at room temperature for three hours. The reaction medium was poured into water, extracted with ethyl acetate, the organic phase decanted off, dried over magnesium sulfate and evaporated.

The residue obtained was purified by chromatography on a silica column eluted with a mixture of heptane and ethyl acetate (90/10). After evaporation of the solvents, 307 mg (41%) of the expected ethyl amide of melting point 223–4° C. were recovered.

EXAMPLE 26

Preparation of N-4-hydroxyphenyl-4-(3,5,5,8,8-pentamethyl-5,6,7,8-tetrahydro-2-nalhthylthio)benzamide:

(a) Synthesis of N-4-acetoxymhenyl-4-naphthylthio)benzamide:

In a manner similar to Example 25(b), by the reaction of 735 mg (2 mmol) of 4-(3,5,5,8,8-pentamethyl-5,6,7,8-tetrahydro-2-naphthylthio)benzoyl chloride with 900 mg (6 mmol) of 4-aminobenzyl acetate, 250 mg (26%) of the expected amide of melting point 186–7° C. were obtained.

(b) Synthesis of N-4-hydroxyphenyl -4-(3,5,5,8,8-pentamethyl-5,6,7,8-tetrahydro-2-naphthylthio)benzamide:

In a manner similar to Example 2 (a), starting with 100 mg (0.2 mmol) of N-4-acetoxyphenyl-4-(3,5,5,8,8-pentamethyl-5,6,7,8-tetrahydro-2-naphthylthio)benzamide, 65 mg (71%) of the expected compound of melting point 236–7° C. were obtained.

EXAMPLE 27

In this example, various specific formulations based on the compounds according to the invention are illustrated.

(A) ORAL ROUTE:

(a) 0.2 q Tablet:

| (i) | Compound prepared in Example 7 | 0.001 g |
|---|---|---|
| (ii) | Starch | 0.114 g |
| (iii) | Dicalcium phosphate | 0.020 g |
| (iv) | Silica | 0.020 g |
| (v) | Lactose | 0.030 g |
| (vi) | Talc | 0.010 g |
| (vi) | Magnesium stearate | 0.005 g |

(b) Oral suspension in 10 ml ampoules:

| (i) | Compound of Example 8 | 0.05 g |
|---|---|---|
| (ii) | Glycerin | 1.000 g |
| (iii) | Sorbitol at 70% | 1.000 g |
| (iv) | Sodium saccharinate | 0.010 g |

-continued

| (v) | Methyl parahydroxybenzoate | 0.080 g |
|---|---|---|
| (vi) | Flavoring qs | |
| (vii) | Purified water qs | 10 ml |

(B) TOPICAL ROUTE:

(a) Ointment:

| (i) | Compound of Example 8 | 0.020 g |
|---|---|---|
| (ii) | Isopropyl myristate | 81.700 g |
| (iii) | Fluid paraffin oil | 9.100 g |
| (iv) | Silica ("Aerosil 200" marketed by DEGUSSA) | 9.180 g |

(b) Ointment:

| (i) | Compound of Example 9 | 0.300 g |
|---|---|---|
| (ii) | Petroleum jelly qs | 100 g |

(c) Nonionic water-in-oil cream:

| (i) | Compound of Example 7 | 0.100 g |
|---|---|---|
| (ii) | Mixture of emulsified lanolin alcohols, waxes and oils ("anhydrous Eucerin" marketed by BDF) | 39.900 g |
| (iii) | Methyl parahydroxybenzoate | 0.075 g |
| (iv) | Propyl parahydroxybenzoate | 0.075 g |
| (v) | Sterile demineralized water qs | 100 g |

(d) Lotion:

| (i) | Compound of Example 8 | 0.100 g |
|---|---|---|
| (ii) | Polyethylene glycol (PEG 400) | 69.900 g |
| (iii) | Ethanol at 95% | 30.000 g |

(e) Hydrophobic ointment:

| (i) | Compound of Example 7 | 0.300 g |
|---|---|---|
| (ii) | Isopropyl myristate | 36.400 g |
| (iii) | Silicone oil ("Rhodorsil 47 V 300" marketed by RHôNE-POULENC) | 36.400 g |
| (iv) | Beeswax | 13.600 g |
| (v) | Silicone oil ("Abil 300.000 cst" marketed by GOLDSCHMIDT) qs | 100 g |

(f) Nonionic oil-in-water cream:

| (i) | Compound of Example 7 | 0.500 g |
|---|---|---|
| (ii) | Cetyl alcohol | 4.000 g |
| (iii) | Glycerol monostearate | 2.500 g |
| (iv) | PEG 50 stearate | 2.500 g |
| (v) | Shea butter | 9.200 g |
| (vi) | Propylene glycol | 2.000 g |
| (vii) | Methyl parahydroxybenzoate | 0.075 g |

| | | |
|---|---|---|
| (viii) | Propyl parahydroxybenzoate | 0.075 g |
| (ix) | Sterile demineralized water qs | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A polycyclic aromatic compound having the structural formula (I):

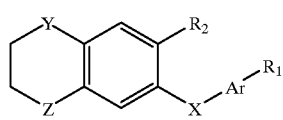

(I)

in which $R_1$ is a hydrogen atom, a —$CH_3$ radical, a —$CH_2$—O—$R_3$ radical, a —$CH_2$—O—CO—$R_4$ radical, an —O—$R_5$ radical, an —O—(—CH2-)$_m$-(—CO—)$_n$-$R_6$ radical, a —CO—$R_7$ radical, a —CO—O—$R_8$ radical or an —S(O)$_p$—$R_9$ radical, wherein m, n, p and the radicals $R_3$ to $R_9$ are as defined below; $R_2$ is a hydrogen atom or a halogen atom, a lower allyl radical, an —$NO_2$ radical, an —O—$COR_4$ radical, an —$OR_9$ radical or a radical:

wherein the radicals $R_4$, $R_9$ and $R_{10}$ are as defined below; Ar is a radical selected from the following formulae:

(d)

X is —O—, —S(O)$_t$- or an —$NR_9$- radical wherein I is as defined below; Y and Z are each —O—, —S(O)$_t$-or a radical —$CR_{11}R_{12}$, wherein the radicals $R_{11}$ and $R_{12}$ are as defined below; m is an integer equal to 1, 2 or 3. n is an integer equal to 0 or 1; p is an integer equal to 0, 1, 2 or 3; t is an integer equal to 0, 1 or 2; $R_3$ is a hydrogen atom or a lower alkl radical; $R_4$ is a lower alkyl radical; $R_5$ is a hydrogen atom or a lower alkyl radical; & is a lower alkyl radical or a heterocycle; $R_7$ is a hydrogen atom, a lower alkyl radical or a radical:

in which R' and R", which may be identical or different, are each a hydrogen atom, a lower alkyl radical, a mono- or polyhydroxyallyl radical, an optionally substituted aryl radical, or an amino acid or peptide or sugar residue, with the proviso that R' and R" may together form, with the nitrogen atom from which they depend, a nitrogen-containing heterocycle; $R_8$ is a hydrogen atom, a linear or branched alkyl radical having from 1 to 20 carbon atoms, an alkenyl radical, a mono- or polyhydroxyalkyl radical, an optionally substituted aryl or aralkyl radical or a sugar residue or an amino acid or peptide residue; $R_9$ is a hydrogen atom or a lower alkyl radical; $R_{10}$ is a hydrogen atom or a lower alkyl radical; $R_{11}$ is a hydrogen atom or a lower alkyl radical; $R_{12}$ is a hydrogen atom or a lower alkyl radical; with the proviso that Y and Z cannot at the same time each be an oxygen atom or an —S(O)$_t$- radical; or a pharmaceutically/cosmetically acceptable salt or optical or geometric isomer thereof.

2. A polycyclic aromatic compound as defined by claim 1, comprising a pharmaceutically acceptable salt thereof.

3. A polycyclic aromatic compound as defined by claim 1, wherein formula (I), the lower alkyl radical substituents are selected from the group consisting of methyl, ethyl, isopropyl, butyl, tert-butyl and hexyl radicals.

4. A polycyclic aromatic compound as defined by claim 1, wherein formula (I), the linear or branched alkyl radical substituents having from 1 to 20 carbon atoms are selected from the group consisting of methyl, ethyl, propyl, 2-ethylhexyl, octyl, dodecyl, hexadecyl and octadecyl radicals.

5. A polycyclic aromatic compound as defined by claim 1, wherein formula (I), the monohydroxyalkyl radical substituents are selected from the group consistng of 2-hydroxypropyl and 3-hydroxypropyl radicals.

6. A polycyclic aromatic compound as defined by claim 1, wherein formula (I), the polyhydroxyalkyl radical substituents are selected from the group consisting of 2,3-dihydroxypropyl, 2,3,4-trihydroxybutyl, 2,3,4,5-tetrahydroxypentyl and pentaerythritol radicals.

7. A polycyclic aromatic compound as defined by claim 1, wherein formula (I), the aryl radical substituents are selected from the group consisting of phenyl radicals optionally substituted by at least one halogen atom, or a hydroxyl or nitro functional group.

8. A polycyclic aromatic compound as defined by claim 1, wherein formula (I), the aralkyl radical substituents are selected from the group consisting of benzyl and phenethyl radicals optionally substituted by at least one halogen atom, or a hydroxyl or nitro functional group.

9. A polycyclic aromatic compound as defined by claim 1, wherein formula (I), the alkenyl radical substituents have from 2 to 5 carbon atoms and comprise at least one site of ethylenic unsaturation.

10. A polycyclic aromatic compound as defined by claim 1, wherein formula (I), the sugar residue substituents are selected from among those of glucose, galactose, mannose and glucuronic acid.

11. A polycyclic aromatic compound as defined by claim 1, wherein formula (I), the amino acid residue substituents are selected from among those of lysine, glycine and aspartic acid.

12. A polycyclic aromatic compound as defined by claim 1, wherein formula (I), the peptide residue substituents are those of a dipeptide or tripeptide.

13. A polycyclic aromatic compound as defined by claim 1, wherein formula (I), the heterocyclic radical substituents are selected from among piperidino, morpholino, pyrrolidino and piperazino radicals which are optionally substituted by a $C_1$–$C_6$ alkyl radical or a mono- or polyhydroxyalkyl radical.

14. A polycyclic aromatic compound as defined by claim 1, wherein formula (I), the halogen atom substituents are selected from the group consisting of fluorine, chlorine and bromine atoms.

15. A polycyclic aromatic compound as defined by claim 7 comprising an alkali or alkaline earth metal, zinc or amine salt.

16. A polycyclic aromatic compound as defined by claim 1, wherein formula (I), at least one of the following definitions exist:

$R_1$ is a —CO—R, radical;
$R_2$ is a lower alkyl radical or an —$OR_9$ radical;
Ar is a radical of formula (a); and
X is —O—, —S— or —NR9-.

17. A pharmaceutical composition of matter, comprising a therapeutically effective amount of a polycyclic aromatic compound as defined by claim 1, or pharmaceutically acceptable salt or isomer thereof, and a pharmaceutically acceptable vehicle, carrier or diluent therefor.

18. The pharmaceutical composition as defined by claim 17, further comprising a retinoid compound, a D vitamin or derivative thereof, a corticosteroid, an anti-free radical agent, an $\alpha$-hydroxy or $\alpha$-keto acid or derivative thereof, an ion channel blocker, or combination thereof.

19. The pharmaceutical composition as defined by claim 17, comprising a tablet, a capsule, a syrup, a dragee, a suspension, an elixir, a solution, a powder, granules, an emulsion, microspheres, nanospheres, lipid vesicles, polymeric vesicles, or an injectable.

20. The pharmaceutical composition as defined by claim 17, comprising an ointment, a cream, a milk, a salve, an impregnated pad, a gel, a spray, or a lotion.

21. The pharmaceutical composition as defined by claim 17, which is suitable for topical administration.

22. The pharmaceutical composition as defined by claim 17, adopted for systemic administration.

23. The pharmaceutical composition as defined by claim 17, comprising from 0.001% to 5% by weight of said polycyclic aromatic compound, or salt or isomer thereof.

24. A method for treating a keratinization disorder in a mammalian organism in need of such treatment, comprising administering to such organism a therapeutically effective amount of the pharmaceutical composition as defined by claim 17.

25. A method for treating a dermalotogical disorder in a mammalian organism in need of such treatment, comprising administering to such organism a therapeutically effective amount of the pharmaceutical composition as defined by claim 17.

26. A method for treating a ophthalmological disorder in a mammalian organism in need of such treatment, comprising administering to such organism a therapeutically effective amount of the pharmaceutical composition as defined by claim 17.

27. A method for treating skin aging in a mammalian organism in need of such treatment, comprising administering to such organism a therapeutically effective amount of the pharmaceutical composition as defined by claim 17.

28. A method for treating epidermal and/or dermal atrophy in a mammalian organism in need of such treatment, comprising administering to such organism a therapeutically effective amount of the pharmaceutical composition as defined by claim 17.

29. A method for treating a healing disorder in a mammalian organism in need of such treatment, comprising administering to such organism a therapeutically effective amount of the pharmaceutical composition as defined by claim 17.

30. A method for treating a sebaceous function disorder in a mammalian organism in need of such treatment, comprising administering to such organism a therapeutically effective amount of the pharmaceutical composition as defined by claim 17.

31. A method for treating a cancerous or precancerous disease state in a mammalian organism in need of such treatment, comprising administering to such organism a therapeutically effective amount of the pharmaceutical composition as defined by claim 17.

32. A method for treating inflammation in a mammalian organism in need of such treatment, comprising administering to such organism a therapeutically effective amount of the pharmaceutical composition as defined by claim 17.

33. A method for treating a viral infection in a mammalian organism in need of such treatment, comprising administering to such organism a therapeutically effective amount of the pharmaceutical composition as defined by claim 17.

34. A method for treating or preventing alopecia in a mammalian organism in need of such treatment, comprising administering to such organism a therapeutically effective amount of the pharmaceutical composition as defined by claim 17.

35. A method for treating a cardiovascular disorder in a mammalian organism in need of such treatment, comprising administering to such organism a therapeutically effective amount of the pharmaceutical composition as defined by claim 17.

36. A method for treating an immune deficiency in a mammalian organism in need of such treatment, comprising administering to such organism a therapeutically effective amount of the pharmaceutical composition as defined by claim 17.

37. A method for treating a dermatological, rheumatic, respiratory, cardiovascular or ophthalmologic disorder in a mammalian organism in need of such treatment, comprising administering to such organism a therapeutically effective amount of the pharmaceutical composition as defined by claim 17.

38. The method as defined by claim 37, comprising administering to such organism a daily dose of said polycyclic aromatic compound of about 0.01 mg/kg to 100 mg/kg of body wieght thereof.

39. A cosmetic composition of matter, comprising a cosmetically effective amount of a polycyclic aromatic compound as defined by claim 1, or cosmetically acceptable salt or isomer thereof, and a cosmetically acceptable vehicle, carrier or diluent therefor.

40. The cosmetic composition as defined by claim 39, comprising a cream, a milk, a lotion, a gel, an ointment, microspheres, nanospheres, lipid vesicles, polymeric vesicles, a soap, or a shampoo.

41. The cosmetic composition as defined by claim 39, comprising from 0.001% to 3% by weight of said polycyclic aromatic compound, or salt or isomer thereof.

42. The cosmetic composition as defined by claim 39, further comprising a retinoid compound, a D vitamin or derivative thereof, a corticosteroid, an anti-free radical agent, an $\alpha$-hydroxy or $\alpha$-keto acid or derivative thereof, an ion channel blocker, or combination thereof.

43. A method for treating a skin or hair disorder on a mammalian organism in need of such treatment, comprising administering to such organism a cosmetically/therapeutically effective amount of the cosmetic composition as defined by claim 39.

44. The pharmaceutical composition as defined by claim 17, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

45. The pharmaceutical composition as defined by claim 17, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

46. The cosmetic composition by claim 39, further comprising a wetting agent, a depigmenting agent, a moisturizing agent, an emollient, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraynoic or 5,8,11-eicosatrynoic acid or ester or amide thereof, or combination thereof.

47. The cosmetic composition as defined by claim 39, further comprising a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, or combination thereof.

* * * * *